United States Patent
Nagle et al.

[19]

[11] Patent Number: 6,020,575
[45] Date of Patent: Feb. 1, 2000

[54] TEMPERATURE-CONTROLLED CONTAINER WITH HEATING MEANS AND EUTECTIC PACK

[75] Inventors: Robert J. Nagle, Morganville; Edward J.. Beldowicz, Edison, both of N.J.

[73] Assignee: TCP/Reliable Inc., Edison, N.J.

[21] Appl. No.: 09/062,399

[22] Filed: Apr. 20, 1998

[51] Int. Cl.[7] ............... A61F 7/00; H05B 3/60; F25D 3/08; B65D 63/08
[52] U.S. Cl. ............ 219/432; 219/386; 219/430; 219/533; 165/104.21; 206/438; 206/521; 206/586; 206/828; 604/114; 604/291
[58] Field of Search ................. 219/385–387, 219/429, 430, 432, 438, 439, 441, 523, 528, 530, 533, 544, 543, 548; 126/400; 165/104.21, 104.19; 206/438, 521, 523, 586, 828, 570; 604/114, 291; 607/98, 114; 62/457.1, 457.2, 529

[56] References Cited

U.S. PATENT DOCUMENTS

| | | | |
|---|---|---|---|
| 3,607,134 | 9/1971 | McIntyre | 219/386 |
| 3,720,198 | 3/1973 | Laing et al. | 126/400 |
| 4,063,068 | 12/1977 | Johnson et al. | 219/386 |
| 4,145,895 | 3/1979 | Hjertstrand et al. | 62/529 |
| 4,277,357 | 7/1981 | Boardman | 126/400 |
| 4,523,078 | 6/1985 | Lehmann | 219/386 |
| 4,528,439 | 7/1985 | Marney, Jr. et al. | 219/386 |
| 4,530,816 | 7/1985 | Douglas-Hamilton | 62/457.2 |
| 4,596,250 | 6/1986 | Beisang III et al. | 607/114 |
| 4,958,506 | 9/1990 | Guilhem et al. | 62/457.2 |
| 5,040,678 | 8/1991 | Lenmark Sr. et al. | 206/523 |
| 5,115,917 | 5/1992 | Schrage | 206/586 |
| 5,235,819 | 8/1993 | Bruce | 62/457.2 |
| 5,317,132 | 5/1994 | Clough et al. | 219/543 |
| 5,417,082 | 5/1995 | Foster et al. | 62/457.1 |
| 5,432,322 | 7/1995 | Ingram et al. | 219/528 |
| 5,477,033 | 12/1995 | Bergholtz | 219/528 |
| 5,586,214 | 12/1996 | Eckman | 219/523 |
| 5,588,531 | 12/1996 | Yoshida et al. | 206/523 |
| 5,647,226 | 7/1997 | Scaringe et al. | 62/457.2 |
| 5,772,037 | 6/1998 | Hurley | 206/586 |
| 5,884,006 | 3/1999 | Frohlich et al. | 219/387 |

*Primary Examiner*—Joseph Pelham
*Attorney, Agent, or Firm*—Jonathan B. Schafrann

[57] ABSTRACT

A temperature-controlled container for transporting biologic tissue and human skin is set out wherein an outer insulated container houses a power source, a thermostat means, a heating means, a power source and interior container along with a retention means for holding the sample in place and a lid that interlocks with the open elongated chamber area by a T-shaped friction plug. The thermostat means may be a microchip and heating element so that the sample and interior temperature does not vary from a given temperature parameter. A eutectic pack which is a solid at room temperature and experiences a phase change to the liquid state at temperatures exceeding room temperature is provided to insure that a minimal super-ambient temperature is maintained.

27 Claims, 4 Drawing Sheets

TEMPERATURE-CONTROLLED CONTAINER WITH HEATING MEANS AND EUTECTIC PACK

FIELD OF THE INVENTION

The present invention generally relates to shipping containers, and more specifically to temperature controlled containers for shipping biologic and other temperature-sensitive materials where a heating element to influence interior temperature is strategically interposed.

BACKGROUND AND SUMMARY OF THE INVENTION

As medical techniques, biologic materials and pharmaceutical preparations have become more sophisticated, numerous problems inherent in their being shipped arises. One such problem area relates to the shipment and preservation of human tissue or human organs and more specifically human skin. When attempting to transport living tissue and specifically human skin, the contents of the shipment must be maintained within a narrow temperature range, which is preferably from about 92° F. to 104° F. Notwithstanding the restrictive temperature window, there are many problems inherent in shipping human skin. Human skin is a fragile structure, being labile to vibratory and mechanical damage. Shipping or transporting human skin, also requires that the skin specimen itself resides submerged in a liquid, nutrient-rich broth. In this condition the tissue sample continues to feed and maintain its viability. Failure to maintain the temperature range without exception results in loss of the tissue sample. For the burn patient or any patient undergoing a skin-graft operation, the patient may lose his/her opportunity for undergoing a life-saving procedure.

Therefore, there has been a recognized longstanding need for furnishing a temperature-controlled container for shipping human tissue. The container must enable the manufacturer, shipper, warehouseman and end-user to ensure the safe delivery of the skin or tissue product. From industry experience, it has been further recognized that human tissue materials retained within such a container must not only be maintained at very specific temperatures but also free from shock and vibration. It should be noted that the prior art presents a multitude of cryogenically maintained transport and storage containers.

The prior art presents a diverse array of temperature-maintained containers. Containers in accordance with the prior art run the gamut from what amounts to an insulated pizza delivery box, on the one hand, to a sophisticated temperature-controlled container the size of a "steamer" trunk on the other. Obviously, such designs fall outside of dimensional and weight parameters necessary for shipping through accepted channels. Overnight and courier delivery services are not readily equipped to deliver oversized containers or containers that require special power needs.

The main problem heretofore remaining unsolved, appertains to a container that maintains a desired temperature range while remaining maneuverable, low in cost, dimensionally acceptable to transport and later storage, and without the need for supervision or intervention during shipping. The desired container must be temperature controllable and provide a specific interior temperature for a prescribed number of hours. Being temperature-controlled is one quality, but being shock resistant is essential.

Given the facility that the medical profession has for being able to utilize human tissues and organs, it is now desirable to increase the amount of time between, transport, storage and use of the biologic materials. Therefore, it is highly desirable to provide a temperature-controlled container that will allow the user to store, transport and ultimately use the material over a period of time which can be measured in terms of days as opposed to minutes and hours. Thus, the need for intricate hand delivery and human failure is minimized by allowing for the tissue to be shipped over longer distances and time periods.

U.S. Pat. No. 4,723,974 issued to Ammerman discloses a container for transporting an amputated extremity by utilizing a flexible walled inner container mounted inside of a flexible walled outer container. The space within the outer and inner walls of the outer and inner containers is filled with a chemical that, when activated, causes a significant reduction in temperature of the environment located within the inner container. The amputated part is maintained in a saline solution and covers the same. It is disclosed that the amputated sample appendage is to be maintained at a sub-ambient temperature.

U.S. Pat. No. 5,040,678 issued to Lenmark discloses a container for transporting biologicals where there is essentially a box within a box construction. A block adds to the shock absorbing qualities.

U.S. Pat. No. 4,145,895 issued to Hjerstraud et al discloses a box within a box design wherein a coolant material like deuterium oxide, undecyl cyanide, 4-bromo-decanoic acid and 2 bromo-decanoic acid is used to maintain the contents in a sub-ambient or cold condition.

U.S. Pat. No. 4,630,448 issued to Blistad discloses a wide-mouthed flexible, collapsible, sterile bag made of sheeting of poly(ethylene vinyl acetate) for storing and shipping solid living tissue at very low temperatures. The thrust of the disclosure resides in maintaining the sterile bag flexible and intact at cryogenic temperatures.

U.S. Pat. No. 4,530,816 issued to Hamilton discloses a method and device for shipping biologic materials within a preferred temperature range of from 4° C. to 10° C., that is near but above freezing. The sample must not be exposed to a temperature of less than 0° C. An isothermal cup or Dewars Flask retains the sample and gelatinized ice retained in a metal container provides the cooling media.

U.S. Pat. No. 4,502,295 issued to Pereyra discloses a storage unit for maintaining organs in a hypothermic environment, within a temperature range of from 0° C. to 7° C., by utilizing a series of containers within containers. The most important feature is the sub-ambient condition within which the sample is maintained. An inner container provides a receptacle for ice thereby maintaining a cold environment.

U.S. Pat. No. 4,958,506 issued to Gulham discloses a container for transporting grafts wherein a constant temperature equal to +4° C. is maintained for 10 hours given an ambient temperature which is "normal." The system uses a thermal exchanger that is charged with a gas like butane.

U.S. Pat. No. 4,986,076 issued to Kirk et al discloses the method of using an endothermic salt to maintain low temperature environment.

Notwithstanding the foregoing art that teaches low temperature maintenance, there is a recognized longstanding need for a container to transport biological materials at elevated temperatures. It should be noted that a container capable of such super-ambient parameters, while also being shock resistant and amenable to shipping through normal shipping channels is not described in the art. In addition, while various forms of container-heaters have been tried, there has been no effective means of using a heater to provide continuous interior container temperatures within a few degrees of tolerance while maintaining physical and cost parameters.

Therefore, the principal object of the present is to provide a temperature controlled container for transporting human tissue at a specific temperature range.

Another object of the present invention is to provide a temperature controlled container where the interior temperature may be maintained at a super ambient level of from 60° F. to 110° F. for at least 120 hours.

A further object of the present invention is to employ a sensitive heating, and thermostat means to influence the interior container temperature to thereby maintain a constant inner temperature at a desired temperature within four degrees from a set temperature.

Yet another object of the present invention is to provide an insulated temperature-controlled container capable of retaining a fragile sample and frangible container in an undamaged condition.

Another object of the present invention is to provide a heating means to modify and maintain interior container temperature in a less cold condition.

A central object of the present invention is to provide a eutectic pack to act as a heat sink in absorbing heat energy to assist in maintaining the contents of the container within a desired temperature range.

Another object of the present invention is to provide a eutectic pack that may be preheated to release heat energy or act as a heat absorbing heat sink in the unheated condition.

The instant invention provides a container adapted to retain a biologic sample like human tissue, and more specifically human skin at a desired temperature range of from 92° F. to 104° F. for a period of at least 120 hours. To implement this end, an outer insulated container is provided with upstanding insulated walls, an insulated base and an insulated lid which nest by means of a friction plug and T-joint within the uppermost boundary of the elongated chamber created by the upstanding wall and base. A power source is disposed within a recessed power source retention area. From the power source, and through leads the power is transmitted to a thermostat means and to a heating means. The heating means is in intimate communication with an interior sample container. Disposed above the sample container resides a eutectic pack adapted to assist in maintaining the sample at an elevated or critical temperature.

The heating means is preferably in communication with the inner sample container, operates on a low voltage power source sufficient to activate a heating means and is thermostatically controlled so that a specific temperature range (92° F. to 104° F.) is maintained. An outer container is adapted to receive the inner sample container, the outer container being adapted to provide excellent insulation from outside temperatures and prevent mechanical damage to the interior sample container.

The present invention provides an outer insulated container with an insulated wall and insulated bottom creating an inner elongated chamber. An insulated lid means interlocks and reversibly seals the outer container. In the elongated chamber created as the inner area of the outer container an area is provided to retain a power source. The power source is in communication with, and supplies a thermostat means and a heating means. The heating means is preferredly further comprised of a heating means, the heating means being retained in a matrix to present the same in a radial array and is reversibly affixed to an inner container which retains the skin sample. The heating means is actuated by an on/off switch or by completing the connection with the power source. When activated the heating element provides warmth to the inner container which retains the biologic or skin sample and to the inner elongated chamber. A series of isolating shock absorbing means may be in communication with at least the four corners of a common shipping corrugated container and the corresponding corners of the outer container.

The thermostat which may be a microchip, solid state device or mechanical means provides power and therefore heat when it senses that the sample or the surrounding ambient temperature falls below pre-determined levels. The thermostat and heating means provide the user with the ability to maintain super and sub-ambient temperatures and may be used to make chamber temperature less cold or more warm depending on the desired temperature range.

BRIEF DESCRIPTION OF THE DRAWINGS

The accompanying drawings, incorporated in and forming a part of the specification, illustrate several aspects of the invention, and together with the description serve to explain the principles of the invention wherein.

DETAILED DESCRIPTION

Figure 1:
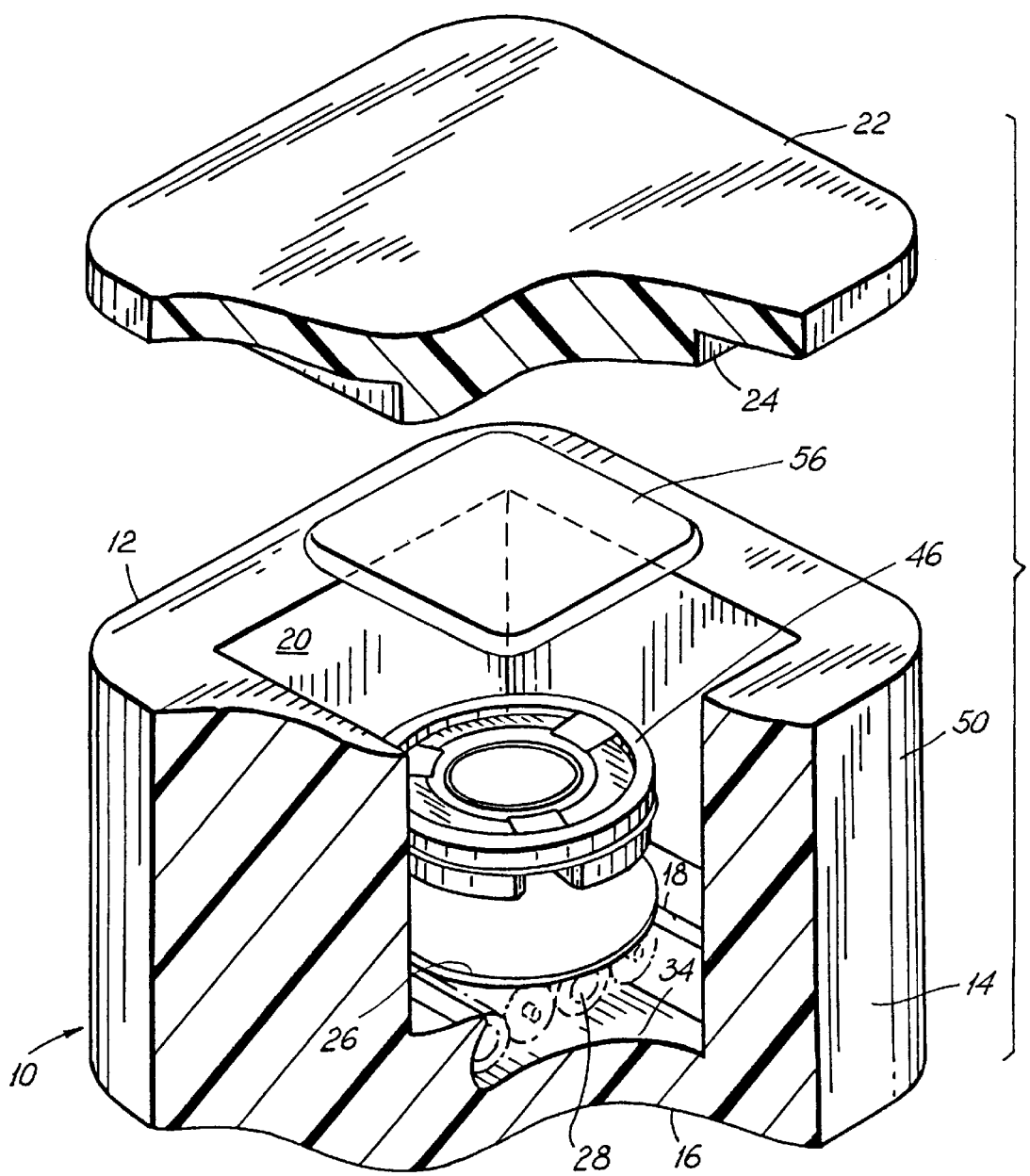
FIG. 1 is a perspective drawing taken as a partial cutaway showing the temperature controlled container with heating means.

Referring with more specificity to the drawings where like numerals refer to like parts temperature-controlled container with heating means throughout, FIG. 1 shows a temperature-controlled container with heating means 10 for transporting materials at pre-set temperatures relative to exterior temperatures.

Figure 2:
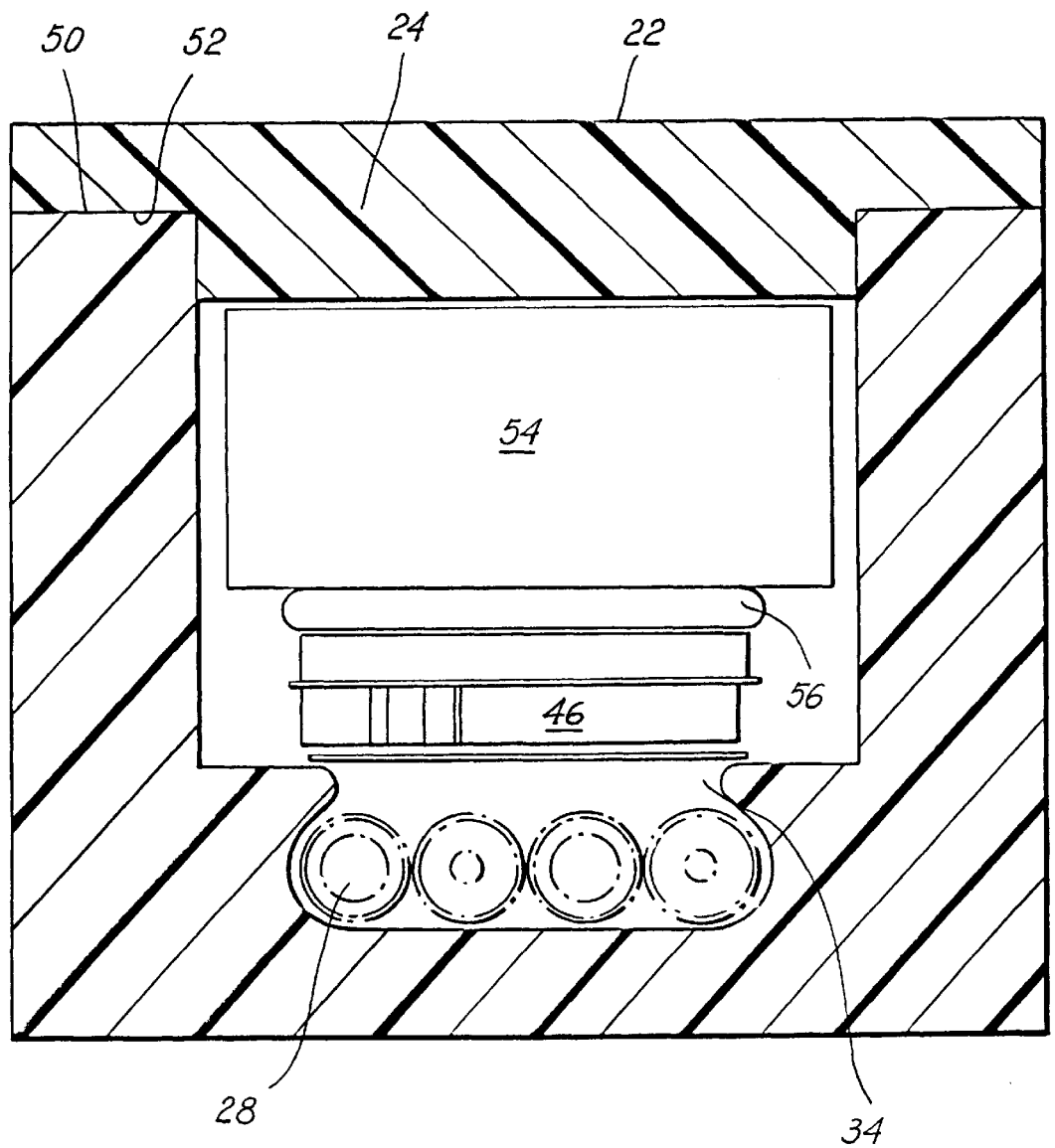
FIG. 2 is an elevational view taken in cross-section showing the temperature-controlled container with heating means in closed condition.

As shown in FIG. 2, temperature controlled container with heating means 10 incorporates an outer container 12 and a lid means 22. In a preferred embodiment, outer container 12 is insulated and for purposes of example shall be termed insulated outer container 12, possesses upstanding insulated wall 14 and an insulated bottom 16. The union of insulated wall 14 and insulated bottom 16 gives rise to inner elongated chamber 48 defined by inner wall surface 20 of insulated wall 14 and 18 of insulated bottom 16.

As depicted in FIG. 1, it is preferred that upstanding insulated wall 14 is comprised of a plurality of upstanding walls sufficient to form a box-shaped enclosure. By modifying the number of walls, changes in geometric shape results from one upstanding wall as in a circular construction to a multi-sided polygon. For purposes of the present invention, four upstanding walls create an overall rectilinear-shaped container. While outer container 12 may be constructed from any material, a light structurally sound and insulating material is preferred. Therefore, it is preferred that outer container 12 be fashioned from a closed cell polymer. The preferred polymers are urethane and expanded polystyrene. The insulating factors for the resulting wall should have R factor based on a two pound density of expand polystyrene which is one inch thick has a K factor for the same which is about 0.23 at 75° F.

As shown in FIGS. 1 and 2, annular chamber 48 defined by inner wall surface 20 of insulated wall 14 and 18, of insulated bottom 16, and provides a discreet area to retain a heating means 26 which includes heating assembly 30, a thermostat and sensing means 32, a power source 28, and inner sample container 46 retaining a temperature sensitive material. Elongated chamber 48 is defined by inner wall surface 20 of insulated wall 14 and 18, of insulated bottom 16, and is approximately seven inches in width, while insulated wall 14 is approximately 2 inches in width. When using expanded polystyrene the 1 to 3.5 ratio of outer wall to inner elongated chamber appears to be operatively preferred. The wall thickness of 2 inches could be reduced with a more efficient polymer or insulating material, although the 2-inch thickness of the wall heightens the overall vibration and shock resistant qualities of the temperature-controlled container with heating means 10.

As most clearly set out in FIG. 2 recessed within insulated bottom 16 and preferably integral therewith is a shallow excavated or recessed retention chamber 34 adapted to receive power source 28. Power source 28 is preferably a battery pack, as for example a series of standard cells, which may be rechargeable. By example in the present invention four C, D cells may be used and dimensionally accommodated. Retention chamber 34, which is preferably fashioned as part of the closed cell bottom 16 insulates power source 28. With power source 28 residing within a recessed cutout the batteries are protected from sub-ambient temperatures while the open top contributes to heating of chamber as heat rises from the batteries. This dynamics is especially advantageous when temperature controlled container 10 is shipped under low temperature conditions. Retention chamber 34 uses the inherent heat from the discharge of power source 28 to maintain a heated atmosphere so that power source 28 will continue to function. Excess heat will dissipate into elongated chamber 48 and beneficially assist in maintaining super ambient temperature conditions.

In accordance with FIG. 1, upstanding wall 14 is in further communication with upstanding walls 14a, 14b, and 14c. While the outer wall surface of upstanding walls 14, 14a, 14b and 14c is flat a planar each corner where said upstanding walls 14, 14a, 14b and 14c meet one another are, in a preferred embodiment, radiused so that radius edge 50 adds an overall oblong character to the otherwise square appearance. By using radius edge 50 a significant amount of weight may be reduced without affecting the insulation factors. A second advantage obtains to the ease of extracting filled temperature-controlled container with heating means 10 from a shipping container like a corrugated box.

As best depicted in FIGS. 1 and 2, constructed from the same closed cell polymeric compound as outer container 12. By milling or molding the lid, depending interlocking lip 24 and upper surface interlocks and fits with the upper area of inner elongated chamber 48 creating a T-shaped friction plug-type joint between lid 22 and outer container 12. FIG. 2 more clearly illustrates the T-shaped friction plug-type joint. Overall, the conformation may further be described as being counter-sunk and interlocking.

Figure 4:
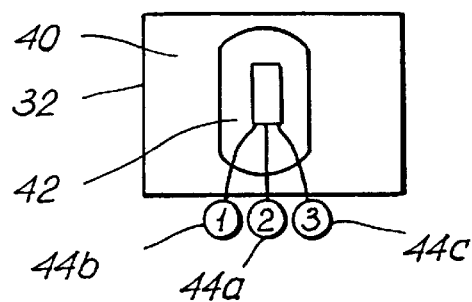
FIG. 4 is a schematic view of the thermostat means.
Figure 5:
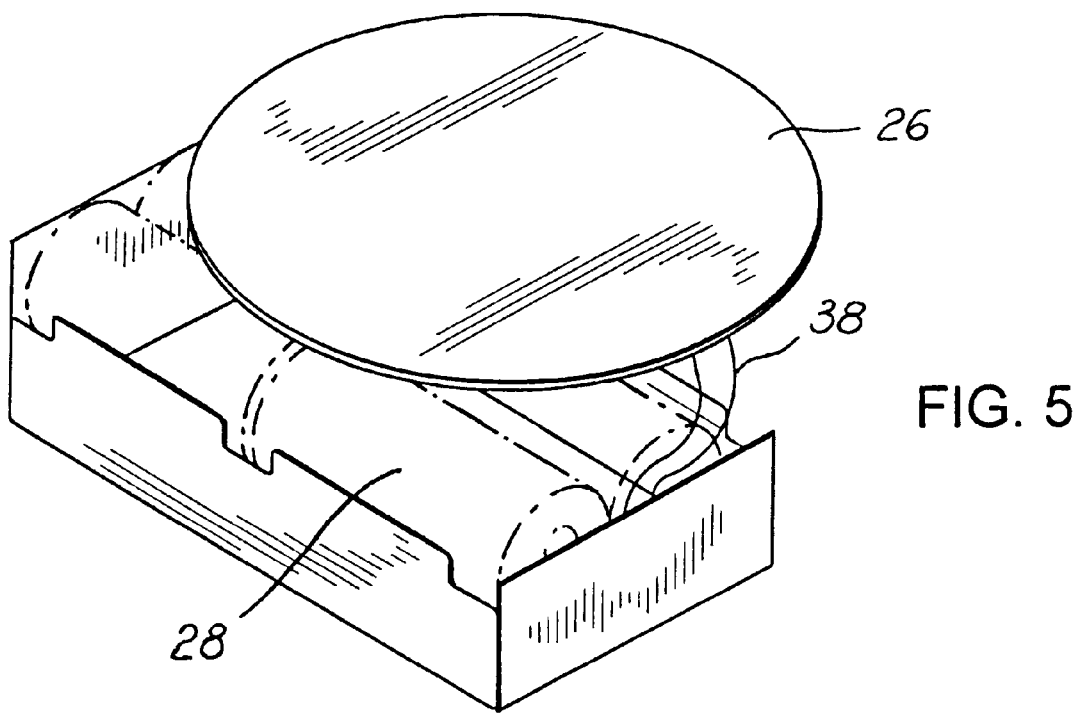
FIG. 5 is a perspective drawing taken as a partial cutaway showing the heating means and power source.

As illustrated by FIG. 5 heating means 26 is preferably powered by a low voltage power means. Power means 28 is preferred to produce from 2 volts to 24 volts of electricity at 0.1 to 1.0 amperes. On/off means 75 which may be a switch or merely a plug connection, when actuated supplies power to heating means 26. As a result of the drawing of power and resulting heating may be almost imperceptible at times, an "on" indicator light 70 like a light-emitting diode may be operatively interposed. In accordance with FIGS. 3,4 and 5 one preferred embodiment, heating means 26 includes, power source 28, heating assembly 30, a thermostat and sensing means 32, lead means 38, heating element 36, on/off means 75, indicator light 70. Heating element 36 may be embedded in a polymer matrix and is in communication with inner sample container 46 as by being reversibly, adhesively affixed.

As described hereinabove, and illustrated by FIGS. 1,2 and 5 the power source may be derived from easily obtainable batteries. For example, a preferred arrangement may include four D-size batteries or four C-size batteries while the indicator light 70 may be a light-emitting diode which takes from 1 to 10 volts to operate. In the present invention, a series of batteries sufficient to comprise 12 ohms and 6 volts will provide sufficient power for a direct current heater and the thermostat chip set out hereinbelow.

Figure 3:
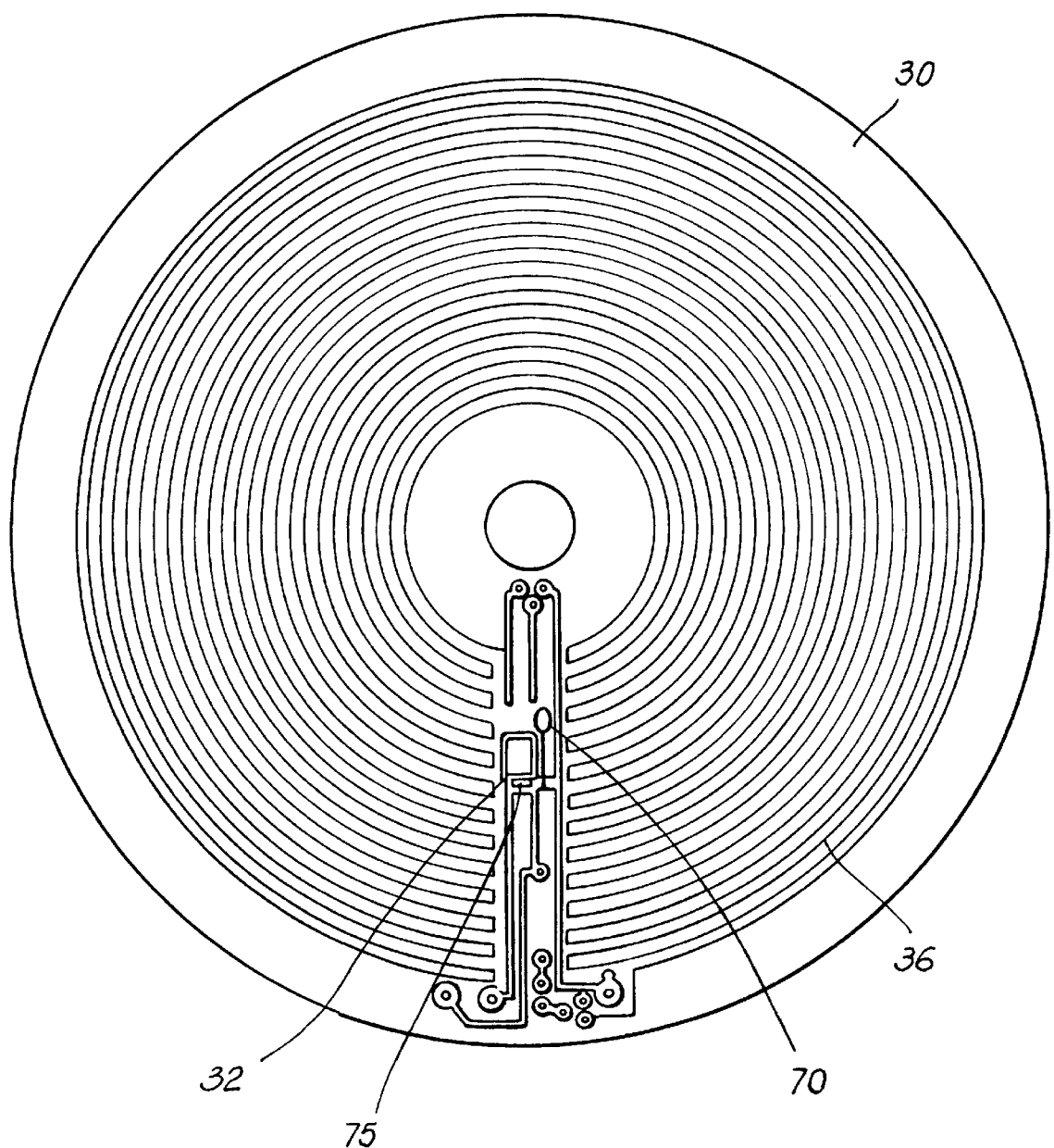
FIG. 3 is a top plan view of the heating means.

FIGS. 3 and 4 show that heating means 26 may be further comprised of a polymer circuit board and a thermostat means. Thermostat means 40 of FIG. 4, may be a bi-metallic strip, a solid state device or microchip. A micro-chip like the model DS1821 thermostat chip (manufactured by Dallas Semi-Conductor Company of Dallas, Tex.) is typical of the microchip or solid state device which may be operatively substituted. Thermostat means 32 should be able to continually sense the surrounding temperature and if positioned in close association inner sample container 46 closely approximates the actual temperatures endured by the sample retained within inner sample container 46. Inner container 46 constructed from glass or a rigid polystyrene or polyvinyl chloride sufficient to maintain its integrity may retain the human skin and rests within outer container 12.

As shown in FIG. 2, a stop means 54 is interposed to prevent inner sample container 46 from dislodging and moving with a force sufficient to damage the tissue or other sample retained therein. It is preferred that an open cell polymer be interposed, said polymer presenting a spongy quality so that it will deform under stress and absorb vibratory energy and shock. Other materials like urethane packing peanuts or bubble wrap can be operatively substituted.

It should be noted that the construction in accordance with the present invention, unlike what has come before, provides constant monitoring of the sample so that immediate compensatory action may be taken in response to changes in temperature. When sample temperature changes markedly, thermostat means 32 completes the circuit which activates heating through heating element 36. It is preferred that heating element 36 is constructed from resistance wire encased in a polymer matrix is in communication with the bottom surface of the inner container to impart additional heat energy when required so that a constant temperature may be maintained. Power source 28 provides energy to heating element 36, the power source being preferably a battery of from 2 volts to 24 volts, and the current passing through the resistance wire generates heat sufficient to influence the temperature within inner elongated chamber 48.

Figure 6:
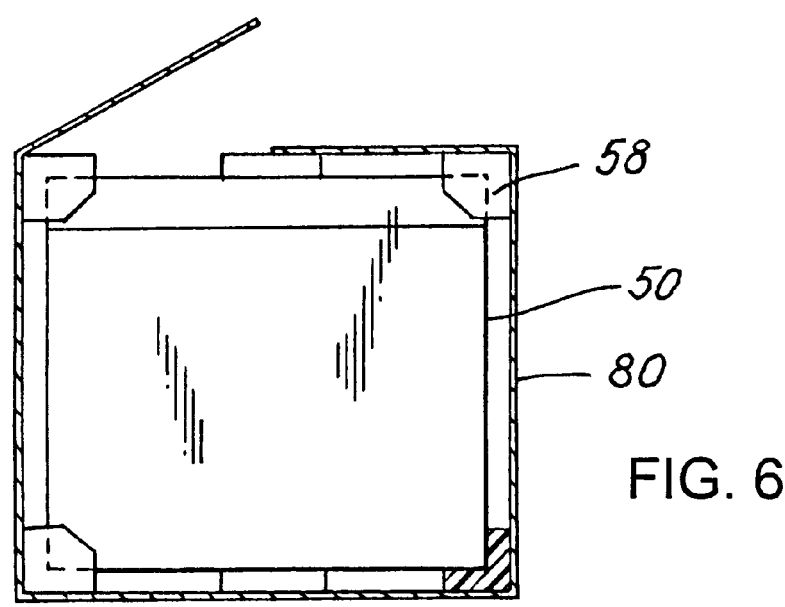
FIG. 6 is an elevational view taken in cross section showing temperature-controlled container with heating means in a closed condition disposed within a corrugated shipping container with shock absorbers disposed therein.

In accordance with FIG. 6, power source 28 is connected to heater means 26 via leads 38. Therefore, in accordance with FIGS. 3,4 and 5, power source 28 through leads 38 supply current to circuit board 40, through legs 44a–44c.

Circuit board 40 is preferably of from 0.03 to 0.06 inches thick and preferably. Heater means 26 also contains an on/off switch 75, a light means 70 and a thermostat means 32. With one lead going to thermostat means 32 and the other to heating element 36 of heating means a circuit is either closed or left open as a sensor means 42 in thermostat means 32 discerns temperatures either outside or within the preset temperature range.

A variety of different polymers may be used for the outer container. It is preferred that the polymers which may be "foamed" to provide a closed cell structure that can be further expanded by entraining. Expanded polymers are given to include a closed cell structure where a gas enlarges the structure by being entrapped therein. The resulting closed cell foams are rigid and possess a thermal conductivity which is somewhat higher than the entrapped gas. A preferred gas for purposes of the present invention is air although hydrogen, oxygen, nitrogen, water vapor, hydrocarbons (ie pentane, methane etc) and fluorocarbons may be operatively substituted. A preferred polymer is expanded polystyrene, but polyurethane, polyvinyl chloride, polycarbonates, polyisocyanates, certain phenolics, sulfones, and polyesters are capable of creating a closed cell structure are suitable. Expanded polystyrene is preferred due to its benign environmental aspects, mechanical strength and insulation qualities.

It has been found that by using a radius-type edge significant weight savings can be achieved without a loss in insulating factors. When using a two pound density expanded polystyrene for outer container 12 having a wall thickness of about two inches a radius may be cut on each of the four corners so that a weight savings of about 5% to about 10% may be achieved. As depicted in FIG. 6, the radiused edge 50 adds further clearance at the corners to prevent contact with the surfaces of corrugated outer container 12 if there is an instance of jarring and shock.

Inner container 46 which holds a human skin sample is further fashioned from a hard polymer or glass material to retain a piece of human skin in a nutrient-rich broth. Inner container 46 is not only non-porous but in many instances frangible, as in the case of a glass container, like a Petri dish. While inner container 46 may be of many sizes, inner elongated chamber 48 would be reduced concomitant therewith. Accommodating inner container 46 which retains, human skin maintained at 92° F.–104° F. and immersed in an aqueous bath of saline and nutrients (so that the skin may continue to feed and remain viable) is unique to the design in accordance herewith.

As set out in FIG. 2, retention means 54 lessens the likelihood of inner container 46 suffering mechanical damage from vibration, shock and impact during shipping. Retention means 54 may be constructed from an open cell polymer. The open cell structure unlike the closed cell structure of the wall means 12 has only some rigidity, and therefore great deformation qualities and makes an ideal cushion. A preferred retention means is an open cell foam block, but other retention means are "Styrofoam" peanuts and bubble wrap. A flexible open cell foam such as polyurethane may be operatively substituted.

As best depicted in FIG. 6 a corrugated box 80 which is, drawn but not claimed as part of the instant invention, removably accepts temperature-controlled container with heating means 10 and isolating shock absorbers 58. Shock absorbers 58 abut each corner of radius edge 50 and are retained therein by the mechanical pressure exerted by the memory of the deformed material. It is preferred that an open-cell polymer be used since its flexibility, compressibility, heightened shock absorbency, economic price, ease of manufacture, and light weight make it an ideal material. The most preferred material is a polyurethane or polyvinylchloride open cell flexible foam material. The pore size varies in accordance with material and method of manufacture, although a spongy deformable consistency is preferred.

In accordance with FIG. 6 there would be a total of ten polyurethane shock absorbers, four in each of the bottom corners, four in each top corner, one in the center of the bottom area and one directly below the flaps of the top area. A corrugated container would enshroud temperature-controlled container with heating means 10 and retain the same during shipping and storage.

Perhaps one of the most advantageous uses for temperature-controlled container and heating means 10 appertains to keeping various temperature-labile materials cold but safeguarding the same from freezing or enduring temperatures that are at or near freezing. In this instance heating means 26 may be used as a temperature moderating means to prevent the inner temperature of elongated chamber 48 from dropping below specified temperatures. Hence, heating means 26 may keep the interior of temperature-controlled container and heating means 10 in a less cold condition. The container in accordance with present invention is specially suited for maintaining temperatures within an overall temperature range of from about 60° F. to 110° F. when the ambient temperature is about room temperature.

In accordance with FIGS. 1 and 2 eutectic pack 56 is preferably positioned above inner sample container 46 and in close association therewith. Eutectic pack 56 as best shown in FIG. 1 further incorporates an impermeable polymer skin surrounding a core preferably comprised of—49% calcium chloride hexahydrate, (CACL2.6H2O) 1% carboxymethylcellulose and the remaining 50% water. This combination is a solid at room temperature with its phase change beginning at about 30 degrees Centigrade. Eutectic pack 56 is an extremely efficient heat sink, absorbing great amounts of heat energy when it is below its phase change temperature. Eutectic pack 56, in its change of phase from solid to liquid, can absorb a great amount of heat energy. Conversely, if pre-heated eutectic pack 56 can provide a significant source for the release of heat energy. Eutectic pack 56 as in the present invention may consist of a ¾ pound 5 inch square polymer package containing calcium chloride hexahydrate, carboxymethylcellulose and water mixture, which is essentially a solid at room temperature, the pack being about one-quarter inch in thickness.

The foregoing description of a preferred embodiment of the present invention has been presented for purposes of illustration and description. It is not intended to be exhaustive or limit the invention to the precise form disclosed. Obvious modifications or variations are possible in light of the above teachings. The embodiments were chosen and described to provide the best illustrations of the principles of the invention and its practical application to thereby enable one skilled in the art to utilize the invention in various embodiments and with various modifications as are suited to the particular use contemplated. All such modifications and variations within the scope of the invention as determined by the appended claims when interpreted in accordance with the breadth to which they are fairly, legally and equitably entitled.

We claim:

1. A temperature-controlled container with heating means comprising:

a. an outer container creating an inner chamber;

b. an inner retention chamber retaining a power source and a sample container;

c. a thermostat means in communication with a power source and an on/off means to restrict or provide power from said power source;

d. a heating means, said heating means in operative communication with said sample container, and said heating means being removably affixed to said sample container; and e. a eutectic pack.

2. The temperature-controlled container with heating means in accordance with claim 1 wherein said outer container further comprises:

a. at least an upstanding insulated wall;

b. an insulated bottom in communication with said insulated wall forming an inner elongated chamber; and c. an insulated lid means.

3. The temperature-controlled container with heating means in accordance with claim 2 wherein said at least an upstanding wall has a plurality of upstanding walls.

4. The temperature-controlled container with heating means in accordance with claim 3 wherein said plurality of upstanding walls has radiused edges.

5. The temperature-controlled container with heating means in accordance with claim 2 wherein said insulated lid means and said upstanding wall means cooperates to form an interlocking T-shaped friction joint.

6. The temperature-controlled container with heating means, in accordance with claim 1 wherein said outer container is further comprised of a closed cell polymeric material.

7. The temperature-controlled container with heating means, in accordance with claim 6 wherein said closed cell polymeric material is expanded polystyrene.

8. The temperature-controlled container with heating means in accordance with claim 7 wherein said closed cell polymeric material is expanded polystyrene having a density of about 2 pounds per cubic foot.

9. The temperature-controlled container with heating means in accordance with claim 1 wherein said power source is at least one battery.

10. The temperature-controlled container with heating means in accordance with claim 1 wherein said heating means is a heating element of resistance wire in a polymer matrix.

11. The temperature-controlled container with heating means in accordance with claim 2 is adapted to be removably affixed to a sample container.

12. The temperature-controlled container with heating means in accordance with claim 1 wherein the thermostat is comprised of a solid state device adapted to insure that a constant temperature is preserved.

13. The temperature-controlled container with heating means in accordance with claim 12 wherein said thermostat is disposed within the heating coil.

14. The temperature-controlled container with heating means in accordance with claim 12 wherein said thermostat is comprised of a micro-chip.

15. The temperature-controlled container with heating means in accordance with claim 11 wherein said thermostat is comprised of a bi-metallic strip.

16. A heating means in accordance with claim 1 comprising:

a. a power source;

b. a switch means controlling the power source;

c. a thermostat means and a heater with a heating element and polymer matrix.

17. A heating means in accordance with claim 16 further comprising said thermostat means located centrally within said heater.

18. A heating means in accordance with claim 17 further comprising said matrix with a series of heating elements being from 0.001 inches to 0.020 inches in thickness.

19. A heating means in accordance with claim 16 further comprising said matrix being further comprised of a thermoplastic polymer.

20. A heating means in accordance with claim 16 further comprising said matrix being further comprised of a metalized polymer sheet.

21. A thermostat means in accordance with claim 1 further comprising:

a. a power source;

b. a lead means from said power source to a heating element, said heating element being retained in a polymer matrix; and c. a second lead means in operative communication with a thermostat means, said thermostat means sensing the temperature ambient thereto and providing power upon the sensing of a specific temperature from said power source to said heating element.

22. The temperature-controlled container with heating means in accordance with claim 1 where a retention chamber retains the power source.

23. The temperature-controlled container with heating means in accordance with claim 1 adapted to be received in a shipping container.

24. The temperature-controlled container with heating means in accordance with claim 23 where an isolated shock absorbing means is in communication with each corner of said temperature-controlled container with heating means.

25. An isolated shock absorbing means in accordance with claim 23 wherein said isolated shock absorbing means is fashioned from an open cell polymeric foam.

26. The eutectic pack in accordance with claim 1 further comprised of calcium chloride hexahydrate, carboxymethylcellulose and water.

27. The eutectic pack in accordance with claim 1 further comprised of 49% calcium chloride hexahydrate, 1% carboxymethylcellulose and 50% water.

* * * * *